United States Patent
Seiler

(10) Patent No.: US 12,241,043 B2
(45) Date of Patent: Mar. 4, 2025

(54) ACTIVE COMPOSITION DELIVERY SYSTEM

(71) Applicant: Dizolve Group Corporation, New Brunswick (CA)

(72) Inventor: Dieter G. Seiler, Ontario (CA)

(73) Assignee: DIZOLVE GROUP CORPORATION, New Brunswick (CA)

( * ) Notice: Subject to any disclaimer, the term of this patent is extended or adjusted under 35 U.S.C. 154(b) by 595 days.

(21) Appl. No.: 17/604,400

(22) PCT Filed: Apr. 17, 2020

(86) PCT No.: PCT/CA2020/000049
§ 371 (c)(1),
(2) Date: Oct. 16, 2021

(87) PCT Pub. No.: WO2020/210893
PCT Pub. Date: Oct. 22, 2020

(65) Prior Publication Data
US 2022/0213416 A1  Jul. 7, 2022

(30) Foreign Application Priority Data

Apr. 17, 2019 (CA) ................................ CA 3040607

(51) Int. Cl.
| | |
|---|---|
| *C11D 17/04* | (2006.01) |
| *A45D 40/00* | (2006.01) |
| *A61K 8/02* | (2006.01) |
| *B65D 65/46* | (2006.01) |
| *C11D 3/37* | (2006.01) |

(Continued)

(52) U.S. Cl.
CPC ............ *C11D 17/044* (2013.01); *A45D 40/00* (2013.01); *C11D 3/3753* (2013.01); *C11D 3/505* (2013.01); *C11D 17/043* (2013.01); *A45D 2040/0093* (2013.01); *A45D 2200/05* (2013.01); *C11D 2111/12* (2024.01)

(58) Field of Classification Search
None
See application file for complete search history.

(56) References Cited

U.S. PATENT DOCUMENTS

| | | |
|---|---|---|
| 5,780,418 A | 7/1998 | Niinaka et al. |
| 10,059,912 B2 | 8/2018 | Cooley et al. |

(Continued)

FOREIGN PATENT DOCUMENTS

WO   WO-2021083599 A1 *  5/2021  ........... C11D 17/045

OTHER PUBLICATIONS

International Search Report for PCT Application No. PCT/CA2020/000049 dated Jul. 2, 2020.

(Continued)

*Primary Examiner* — Lorna M Douyon
(74) *Attorney, Agent, or Firm* — Lippes Mathias LLP

(57) ABSTRACT

An active composition delivery system having a water-soluble top layer, a water-soluble bottom layer, and an active composition disposed therebetween. The water-soluble top and bottom layers are joined together to form a pouch sized and shaped to hold an amount of an active composition. The active composition delivery system further includes a plurality of water-soluble joints, joining the top and bottom water-soluble layers.

39 Claims, 6 Drawing Sheets

(51) Int. Cl.
*C11D 3/50* (2006.01)
*C11D 17/06* (2006.01)

(56) References Cited

U.S. PATENT DOCUMENTS

| | | | |
|---|---|---|---|
| 2002/0169092 A1 | 11/2002 | Alexandre Catlin et al. | |
| 2003/0050209 A1 | 3/2003 | Perkis et al. | |
| 2007/0134304 A1* | 6/2007 | Aubrun-Sonneville | A61Q 19/10 424/443 |
| 2007/0134481 A1* | 6/2007 | Aubrun-Sonneville | A61K 8/0208 428/292.1 |
| 2008/0035174 A1* | 2/2008 | Aubrun-Sonneville | A61Q 19/00 428/305.5 |
| 2013/0053293 A1* | 2/2013 | Dituro | B65D 65/466 510/439 |
| 2013/0244920 A1* | 9/2013 | Lee | C11D 3/2093 510/392 |
| 2017/0298308 A1* | 10/2017 | Labeque | B65D 43/22 |
| 2019/0093057 A1 | 3/2019 | Tan et al. | |

OTHER PUBLICATIONS

Supplementary European Search Report for Application No. EP 20791591 Dated May 5, 2022.

* cited by examiner

ACTIVE COMPOSITION DELIVERY SYSTEM

CROSS-REFERENCE TO RELATED APPLICATIONS

This application is a 371 of PCT Application No. PCT/CA2020/000049, filed Apr. 17, 2020, which claims priority to Canadian Application No. 3,040,607, filed Apr. 17, 2019, the entirety of which is incorporated by reference.

FIELD OF THE INVENTION

The present invention relates to the fields of fabric care, hard surface cleaners, and personal cleaning products. More particularly, the present invention relates to systems and methods for delivering an active composition in the form of a pre-measured dose sufficient for one or more cleaning or treatment operation.

BACKGROUND OF THE INVENTION

Cleaning agents, including detergents, are typically provided in liquid or powder forms. However, users find these forms inconvenient because their use requires an additional step of measuring out a correct dose of the detergent. Apart from the inconvenience of measuring out a correct dose is the material cost associated with the need to provide and store a utensil for measuring out the correct dose, and then load the correct dose, for example, into a dishwasher, a washing machine, or other like washing apparatus. Associated with this requirement for measuring a dose is the risk of getting the dose wrong, and either under-dosing (resulting in poor cleaning action), or over-dosing (resulting in wasted detergent, or damage to the item being cleaned). Other problems associated with liquid and powder forms of cleaning agents are that they are messy, They are also not easily transportable in small quantities, which may be desirable when travelling, for example.

In light of the above noted problems associated with liquid and powder forms of cleaning agents, many users prefer cleaning agents, such as for example, laundry detergents, that are provided in a form that is simpler to use and less messy than the liquid and powder forms.

Attempts have been disclosed In the prior art to overcome some of the above described problems associated with liquid and powder cleaning agents. Some of the attempts included providing a unit dose laundry detergent product, which removed the need to measure out a correct dose of laundry detergent, thereby simplifying for the user the process of loading a washing machine with the correct dose of the laundry detergent.

For example, U.S. Pat. No. 4,356,099 to Davies disclosed fabric treatment products for use in washing machines consisting of a bag formed of water-insoluble, water-impermeable synthetic plastics sheet material containing a fabric treatment composition comprising a liquid fabric treatment composition, such as an aqueous or non-aqueous liquid detergent composition. The bag has a weak seal that will be opened by the mechanical action of a washing machine, to release its liquid detergent contents. However, a problem with the fabric treatment products disclosed by Davies is that they are prone to a failure of the weak seal not opening properly in modern day high efficiency (HE) washing machines. This is because opening of the weak seal in a Davies fabric treatment product relies on the mechanical action of the washing machines, and the more gentle mechanical action of HE washing machined may not be enough to open the bag. Additionally, because the bag is made of a water-insoluble material, it remains in the washing machine during the entire wash cycle, and can affect the cleaning performance if it clings to certain areas of the clothing being washed. Furthermore, the format of the fabric treatment products taught by Davies does not allow for partial doses that may be better suited for laundry loads which are smaller than full loads.

As another example, U.S. Pat. No. 4,188,304 to Clarke discloses a detergent product which comprises a particulate detergent composition contained within a closed water-Insoluble bag which has a water-sensitive seal, whereby the contents of the bag are discharged on contact of the bag with water. Clarke's detergent product shares many of the same problems noted above in connection to Davies. However, an additional problem with the Clarke detergent product is that it is difficult to ensure that all of the particulate detergent composition is emptied out of the bag and fully dissolved in the water, especially if the detergent product is used in the detergent dispensing trays on modern HE washing machines.

As yet another example, laundry detergent pods have become popular in recent years, In which a single pre-measured unit dose of detergent is encapsulated in a water-soluble pouch, typically ranging from 20 to 40 grams in weight. However, a problem associated with such laundry detergent pods is that they do not dissolve readily because the water-soluble pouch covering the detergent powder must dissolve before the water can access the detergent. Furthermore, the detergent is provided as a large mass of partially-compressed powder, which presents a smaller overall surface area for the water to act on. For these reasons, such pods typically do not dissolve fully when used in the detergent dispensing trays on modern HE washing machines.

As yet another example, laundry detergent tablets exhibit similar problems as those described above with respect to laundry detergent pods, due to the large concentrated mass of highly-compressed detergent powder.

In general detergent dispensing trays on modern HE washing machines provide too short a time for dissolving the above noted laundry detergent pods and laundry detergent tables, and so they fail to yield optimal results when used in this way. For this reason, laundry detergent pods are better suited for being placed directly in the washing machine drum to be dissolved during the wash cycle.

Neither the laundry detergent pod, nor the laundry detergent tablet formats allow for partial doses that may be better suited for laundry loads which are smaller than full loads.

As yet another example, U.S. Pat. No. 4,853,142 to Win disclosed a high melting temperature meltblown web, such as a polyester meltblown web, which contains a sufficient amount of condensed liquid detergent to wash a load of laundry and does not exhibit an objectionable sticky feel. Similarly, U.S. Pat. No. 4,938,888 to Kiefer disclosed a cleaning article formed from a detergent composition impregnated into a flexible substrate. The detergent composition includes an alkyl polyglycosides and a detergency builder. The substrates employed are water-insoluble and are solid or substantially solid materials, such as foam, foil, sponge, paper, woven or non-woven cloth.

A problem shared by both Win and Kiefer is that they are made with non-dissolvable substrates, which remain in the washing machine drum after completion of the wash cycle. The non-dissolvable substrates also tend to cling to clothing being washed, making it more difficult for the embedded detergent to dissolve completely. Additionally, non-dissolvable substrates are not compatible with detergent dispensing trays on modern HE washing machines, and both of Win's webs and Kiefer's cleaning articles, impregnated with detergent composition sufficient for a Full load, would be too large to be used efficiently and reliably in the detergent dispensing trays on modern HE washing machines. Additionally, neither Win's web nor Kiefer's cleaning article allow for partial doses that may be better suited for laundry loads which are smaller than full loads.

Other prior art attempts include those disclosed in: U.S. Pat. Nos. 4,374,035; 4,806,261; 5,780,418; 6,756,351; 3,062,030; 6,699,826; 6,831,051; 6,995,126; and 8,669,219; and U.S. Patent Application Publication Nos. 2002/0077265; 2008/0242579; 2010/0035789; 2010/0190677; 2014/0024574; and 2002/0169092.

However, there remains a need for improvements in active composition delivery systems.

SUMMARY OF THE INVENTION

What is desired is an improved system and method for delivering an active composition, such as a cleaning or treatment composition, to where it is needed, that overcomes at least some of the problems in the prior art. For example, what may be desired is a system and method for delivering an active composition in the form of a pre-measured unit dose sufficient for a single cleaning or treatment operation. As another example, what may be desired is a system and method for delivering an active composition with a high actives content. As yet another example, what may be desired Is a system and method for delivering an active composition in a form that is easy to handle and store when dry, yet which dissolves completely when contacted by water, such as, for example, in a washing machine during the laundry cycle, without leaving behind any substrate or noticeable residue.

By way of example, there Is disclosed an active composition delivery system in the form of a laundry detergent article configured to be added to a washing machine to be contacted by water during the laundry cycle. Preferably, the laundry detergent article contains a premeasured unit dose of a powder cleaning composition comprising a laundry detergent, inside a pouch formed from water-soluble sheets sealed together at the edges, to keep the detergent powder from spilling out from the pouch. Preferably, the water-soluble sheets are made of polyvinyl alcohol (PVA). The water-soluble PVA sheets may be sealed together at the edges by, for example, heating, ultrasonic welding, solvent gluing, or sewing with water-soluble PVA thread.

Preferably, the laundry detergent article may include water-soluble stitches through the top and bottom water-soluble sheets, according to an embodiment of the present invention. When included, the water-soluble stitches may be configured to limit the maximum thickness of the laundry detergent article, by contro ling the distribution of the laundry detergent powder inside the pouch. Preferably, the water-soluble stitches may be configured to allow a small gap between the top and bottom water-soluble sheets at each stitch.

The water-soluble stitches may preferably be included in the form of two thread-paths that zig-zag and cross one another over the surface areas of the laundry detergent article in a quilted pattern. Preferably, the quilted pattern will maintain a uniform distribution of the powder cleaning composition within the volume defined by the pouch.

By limiting the maximum thickness of the pouch and controlling the distribution of the laundry detergent powder within the pouch using the water-soluble stitches, according to preferred embodiments of the present invention, the laundry detergent article may be provided in a form resembling a flat sheet, which is aesthetically pleasing, and easy to handle. However, unlike known dissolvable laundry sheets, laundry detergent articles according to the present invention may contain higher amounts of cleaning composition per square inch, enabling more effective cleaning with substantially the same form factor (or the same level of cleaning in a smaller form factor).

By limiting the maximum thickness of the pouch and controlling the distribution of the laundry detergent powder within the pouch using the water-soluble stitches, according to preferred embodiments of the present invention, the laundry detergent article may deliver its cleaning composition contents more rapidly and uniformly in the washing machine, for example. It has been found that by controlling the distribution of the laundry detergent powder, and maintaining an overall flat form of the laundry detergent article with the water-soluble stitches helps to keep the laundry detergent powder spread out over a large surface area, which tends to increase dissolution, and at the same time reduces the type of clumping of the laundry detergent powder, which tends to cause uneven dissolution.

Preferably, the laundry detergent article may include a plurality of pouches attached together at the joined edges. It is contemplated that the size and shape of each pouch may be the same, or alternately, the laundry detergent article may include differently sized, and/or shaped pouches. For example, differently sized, and/or shaped pouches may be included to provide different pre-measured unit doses for the user to select. As another example, the pouches may be configured to allow the user to easily select a combination of pre-measured unit doses for a particular application.

Most preferably, the laundry detergent article may be provided with a frangible member, or line of weakness along some or all of the joined edges separating the pouches from one another, to make it easier for the user to separate and remove one or more pouches from the laundry detergent article, so they may be used.

Although embodiments of the active composition delivery system of the present invention include laundry detergent articles, as mentioned above, the Invention is not limited thereto, but comprehends other applications, depending on the formulations of the active composition, the top and bottom water-soluble sheets, and the water-soluble stitches comprised by the cleaning composition delivery system.

For example, other embodiments of the present invention may include active composition delivery systems, wherein the active composition is a cleaning composition, configured for cleaning body parts (i.e. personal care products), for cleaning dishes and utensils, and for cleaning hard surfaces.

As another example, other embodiments of the present invention may include active composition delivery systems, wherein the active composition is a treatment composition, configured for treating fabric to provide, for example, scent properties (i.e. scent enhancement), fabric softening properties, anti-microbial properties, anti-bacterial properties, anti-fungal properties, insect repellant properties, scent properties, and combinations thereof.

Although embodiments of the active composition delivery system of the present invention include laundry detergent articles, for use in a washing machine, the invention is not limited thereto, but comprehends other manners of use. For example, the active composition delivery system may be configured to enable the user to prepare a volume of a cleaning or treating solution for current use or for later use. For example, the user may dissolve an active composition delivery system in a pail of water and use the solution in the pail together with a mop to clean the floor. As another example, the user may dissolve an active composition delivery system in 8 kitchen sink filled with a volume of water and use the solution to wash dishes. As yet another example, the user may hold an active composition delivery system in his hands under running water to cleanse his hands, and/or other body parts. As yet another example, the user may hold an active composition delivery system in her hands or on her head in the shower to shampoo or condition her hair. As yet another example, the user may dissolve an active composition delivery system in a spray bottle filled with a volume of water and use solution to clean hard surfaces. As yet another example, the user may dissolve an active composition delivery system in a disposable or reusable storage bottle filled with a volume of water and later dispense the solution, on an as needed basis, to use as a liquid fabric softener, a liquid dish detergent, a liquid laundry detergent, or the like.

Therefore, in accordance with one aspect of the present invention, there is disclosed an active composition delivery system comprising:
  at least one water-soluble sheet arranged and joined together to form at least one pouch having a top layer and a bottom layer, and being surrounded by joined edges;
  an active composition disposed in said at least one pouch; and
  a plurality of water-soluble joints joining said top layer and said bottom layer, said water-soluble joints being arranged in a region surrounded by said joined edges, to form two or more compartments, with said active composition being disposed substantially evenly across said two or more compartments;
  wherein said active composition delivery system has a substantially flat, sheet-like shape; and
  wherein said active composition delivery system releases said active composition after being contacted with a sufficient amount of water to dissolve said at least one water-soluble sheet.

According to another aspect of the present invention, there is disclosed a use of said active composition delivery system mentioned above, in a washing machine, wherein said active composition comprises a laundry detergent active or a fabric softener active.

According to yet another aspect of the present invention, there is disclosed a use of said active composition delivery system mentioned above, in a dishwasher, wherein said active composition comprises a dishwasher detergent.

According to yet another aspect of the present invention, there are disclosed a method of making an active composition delivery system, said method comprising the steps of:
  a) arranging and joining at least one water-soluble sheet together to form a tube;
  b) closing one end of said tube with a first transverse joint;
  c) filling at least a portion of said tube with an amount of active composition through an open end of said tube;
  d) closing said tube with a downstream transverse joint spaced a predetermined distance from said first transverse joint, with said active composition disposed between said first transverse joint and said downstream transverse joint to form a pouch, said pouch having said active composition disposed therein, and having a top layer and a bottom layer; and
  e) providing a plurality of water-soluble joints joining said top layer and said bottom layer to form two or more compartments, with said active composition being disposed substantially evenly across said two or more compartments;
  wherein said active composition delivery system has a substantially flat, sheet-like shape; and
  wherein said active composition delivery system releases said active composition after being contacted with a sufficient amount of water to dissolve said at least one water-soluble sheet.

BRIEF DESCRIPTION OF THE DRAWINGS

Reference will now be made to the preferred embodiments of the present invention with reference, by way of example only, to the following drawings in which.

DETAILED DESCRIPTION OF THE PREFERRED EMBODIMENTS

The present invention is described in more detail with reference to exemplary embodiments thereof as shown in the appended drawings. While the present invention is described below including preferred embodiments, it should be understood that the present invention is not limited thereto. Those of ordinary skill in the art having access to the teachings herein will recognize additional implementations, modifications, and embodiments which are within the scope of the present invention as disclosed and claimed herein.

Figure 1:
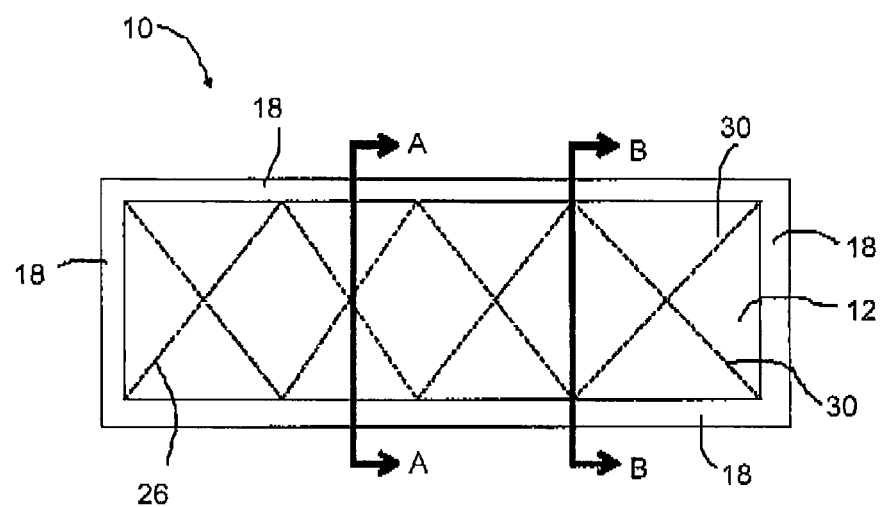
FIG. 1 is a top view of an active composition delivery system according to an embodiment of the present invention.
Figure 2:
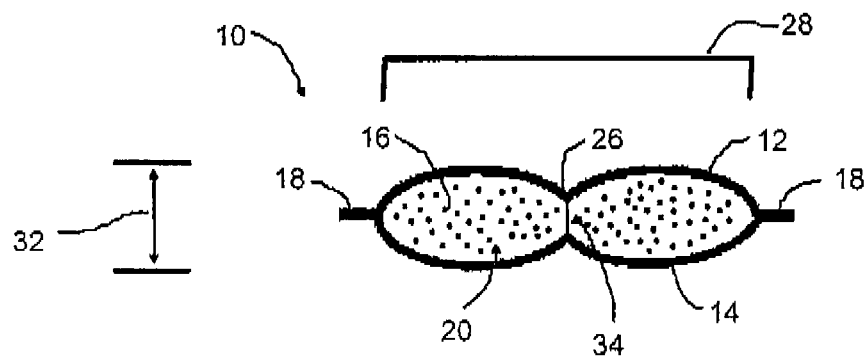
FIG. 2 is a cross-sectional view of the active composition delivery system of FIG. 1 taken along line A-A.
Figure 3:
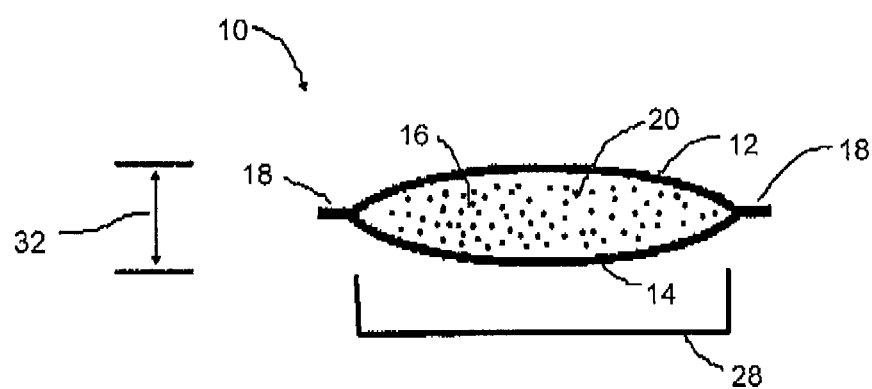
FIG. 3 is a cross-sectional view of the active composition delivery system of FIG. 1 taken along line B-B.

An active composition delivery system 10 according to an embodiment of the present invention is shown in FIGS. 1 to 3. As shown, the active composition delivery system 10 has a top layer 12, a bottom layer 14, and an active composition 16 disposed between the top and bottom layers 12, 14. Preferably, the top and bottom layers 12, 14 are joined together along their edges 18 to contain the active composition 16. What is important is that the top and bottom layers 12, 14, together with their joined edges 18, form a pouch 20, sized and shaped to hold a pre-measured amount of an active composition 16, so that the active composition delivery system 10 may be used for its intended use, as will be discussed in more detail below.

Figure 8:
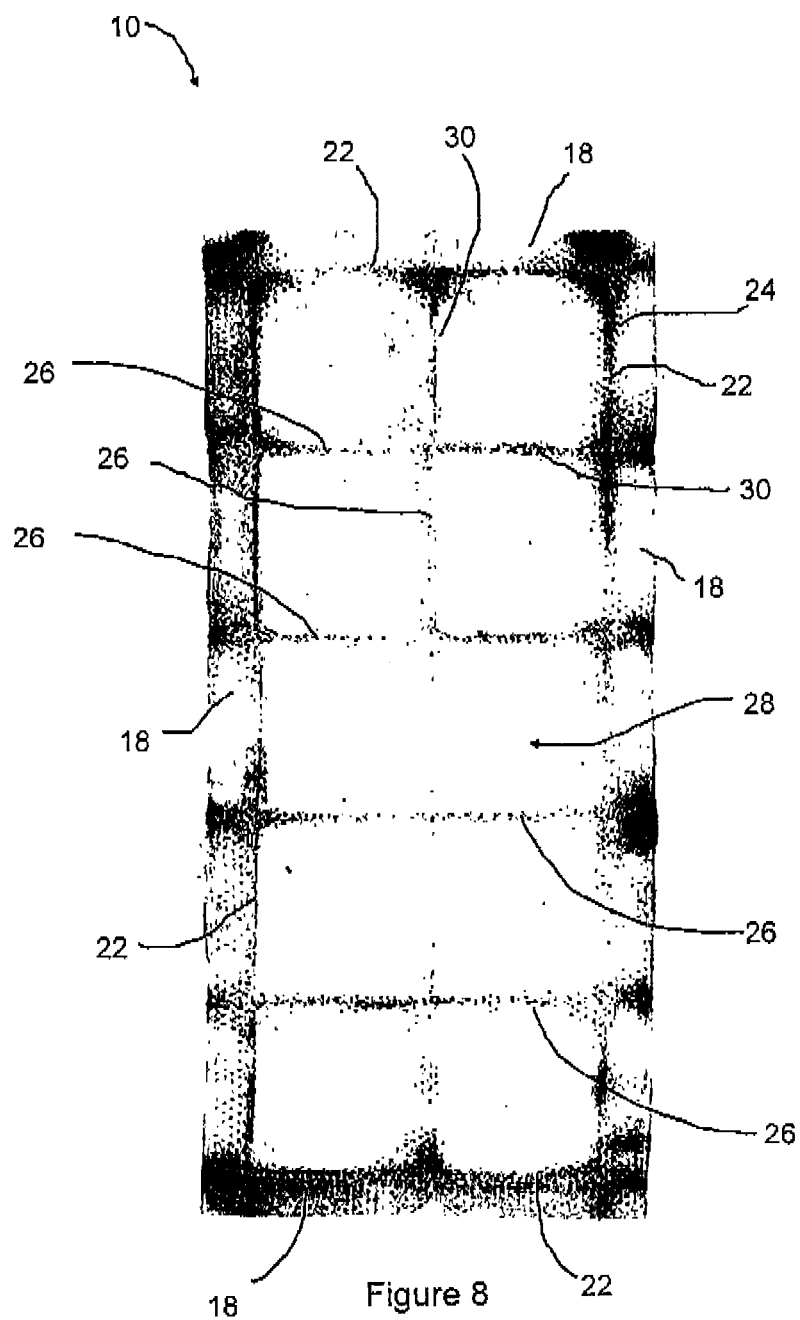
FIG. 8 is a top view of an active composition delivery system according to another embodiment of the present invention.
Figure 9:
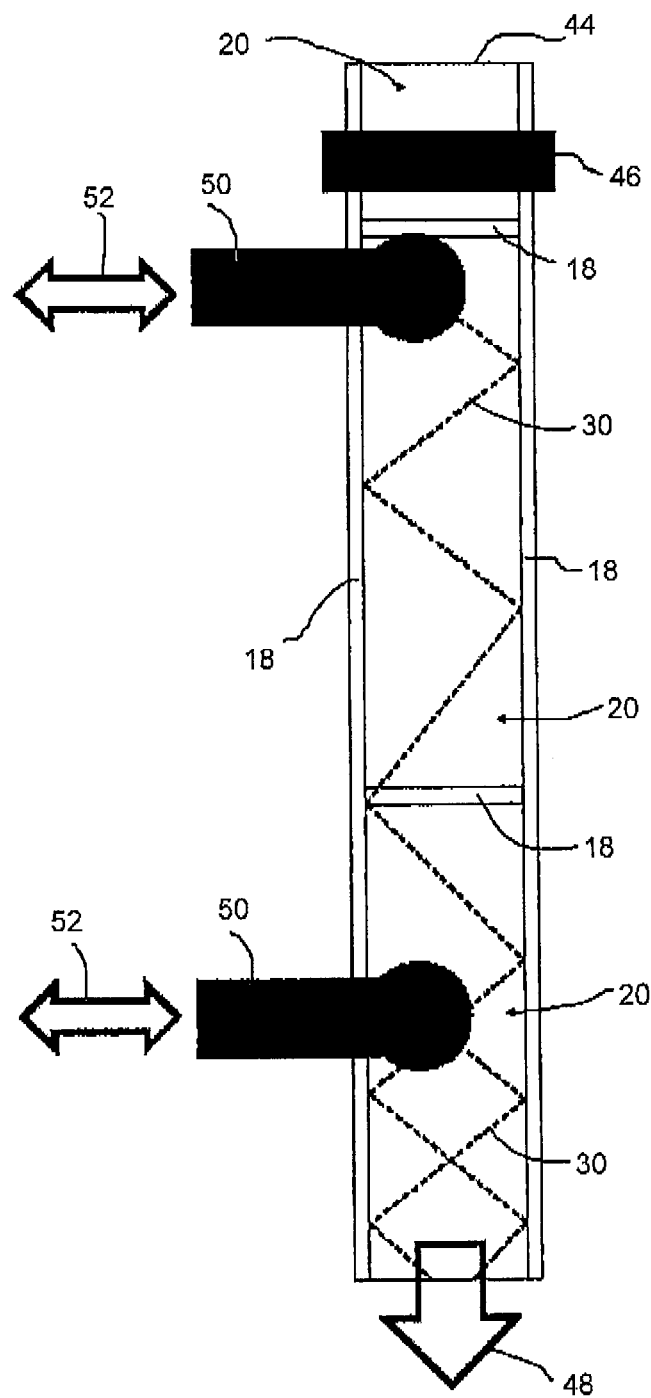
FIG. 9 is a top view of an apparatus for making the active composition delivery system of FIG. 1, according to an embodiment of the present invention.

Preferably, the top and bottom layers 12, 14, are water-soluble sheets made of polyvinyl alcohol (PVA), and the joined edges 18 may be formed by sealing the top and bottom layers 12, 14 together at their edges by, for example, heating, ultrasonic welding, or solvent gluing. As another example, the joined edges 18 may be formed by sewing the top and bottom layers 12, 14 together at their edges with water-soluble thread, which may also be formed from PVA, as shown in FIGS. 8 and 9. It will be appreciated that forming the joined edges 18 by sewing with PVA thread will require using sufficiently tight stitches 22, arranged in a continuous thread path 24 to ensure that the active composition 16 does not spill or leak out of the pouch 20 through gaps between the top and bottom layers 12, 14. Preferably, the PVA thread will be selected to have similar dissolution properties to those of the top and bottom layers 12, 14.

The active composition may also be water-soluble, in which case the active composition delivery system 10 will be completely dissolvable in water. However, according to other embodiments of the present invention, the active composition 16 may be water insoluble, In which case, the active composition delivery system 10 will not be completely dissolvable in water, although only the active composition will remain, for example as a fabric treatment of encapsulated fragrance coating or impregnating portions of the treated fabric.

Although the top and bottom layers 12, 14 may be provided as separate sheets of PVA material, it is also contemplated that they may be provided as a single sheet of material, which is folded over (not shown). In this embodiment of the present invention, one half of the folded sheet of material forms the top layer 12, and the other half of the folded sheet of material forms the bottom layer 14. For the purposes of this description, the fold may be considered one of the joined edges 18. Additionally, the folded edge may be further processed to match the look of the other joined edges, for example by heating, ultrasonic welding, solvent gluing, or sewing. All such embodiments are comprehended by the present invention.

Preferably, the active composition delivery system 10 also includes a plurality of loose stitches 26 joining the top and bottom layers 12, 14 in a region 28 surrounded by the joined edges 18. These loose stitches 26 may be arranged to define one or more thread paths 30 contained in the region 28. Preferably, the one or more thread paths 28 may form a quilted pattern in the region 28, which gives the active composition delivery system 10 an aesthetic look, and pleasing feel. In this regard, FIG. 1 shows, by way of example only, a quilted pattern formed by two zig-zagging thread paths 28 in the region 30 surrounded by the joined edges 18. Although, FIG. 1 shows a quilted pattern consisting substantially of triangles and squares (or diamonds), other quilted patterns are comprehended by the present invention, including those, formed from other rectilinear, and non-rectilinear shapes.

With reference to FIG. 2, it can be seen from this cross-sectional view that the active composition 16 is contained in the pouch 20 formed by the top and bottom layers 12, 14, and their joined edges 18. Additionally, there is shown that the loose stitches 26 are configured and arranged In the region 30 to limit a maximum thickness 32 of the active composition delivery system 10, so that it will have a generally flat, quilted profile. Preferably, the maximum thickness 32 may be ⅛ inch to ⅜ Inch, inclusive. In this regard, the loose stitches 26 may be configured to allow a gap 34 to form between the top and bottom layers 12, 14 at each loose stitch 26. Advantageously, the gaps 34 permit slight movement of the active composition 16 within the pouch 20, which adds flexibility to the active composition delivery system 10. Thus the term "loose stitch" as used herein does not mean that the stitch may be easily undone, but rather that stitch allows the top and bottom layers 12, 14 to be slightly spaced apart to allow a gap 34 to be created, that will help define the maximum thickness 32 of the active composition delivery system 10. However, it is contemplated that the loose stitches 26 in the region 28 between the joined edges 18 may be replaced with tight stitches 22, in other embodiments of the present invention, thereby removing the gaps 34. Accordingly, the loose stitches 26 may preferably be configured to provide a gap 34 with a vertical length of between 0 Inch and ¹⁄₁₆ inch, inclusive. All such embodiments are comprehended by the present invention.

As will now be understood, the water-soluble loose stitches 26 create joints between the top and bottom water-soluble sheets to maintain a flat sheet-like shape of the dissolvable active composition delivery system 10. The joints arranged in the quilted thread-paths 30 limit the maximum thickness 32 of the active composition delivery system 10, and form compartments to control the distribution of active composition 16 contained within the active composition delivery system 10. Preferably, the joints are configured to allow the small gap 34 between the top and bottom layers 12, 14 at each joint. As the active composition delivery system 10 dissolves in water, the active composition Inside is exposed as much as possible in terms of surface area to the water surrounding the active composition delivery system 10. The arrangement helps prevent clumps of active composition that could take longer to dissolve as compared to the thinner flat, sheet-like structure, according to the present invention.

Another advantage of flat, sheet-like structure of the active composition delivery system 10, is that it may be configured to be compatible with automatic dispensers in a new generation of washing machine designs.

It is contemplated that the water-soluble joints, and resulting gaps 34 may be formed by processes other than sewing with water-soluble thread, known in the art, including heating, ultrasonic welding, solvent gluing, and the like. All such embodiments are comprehended by the present Invention.

Figure 4:
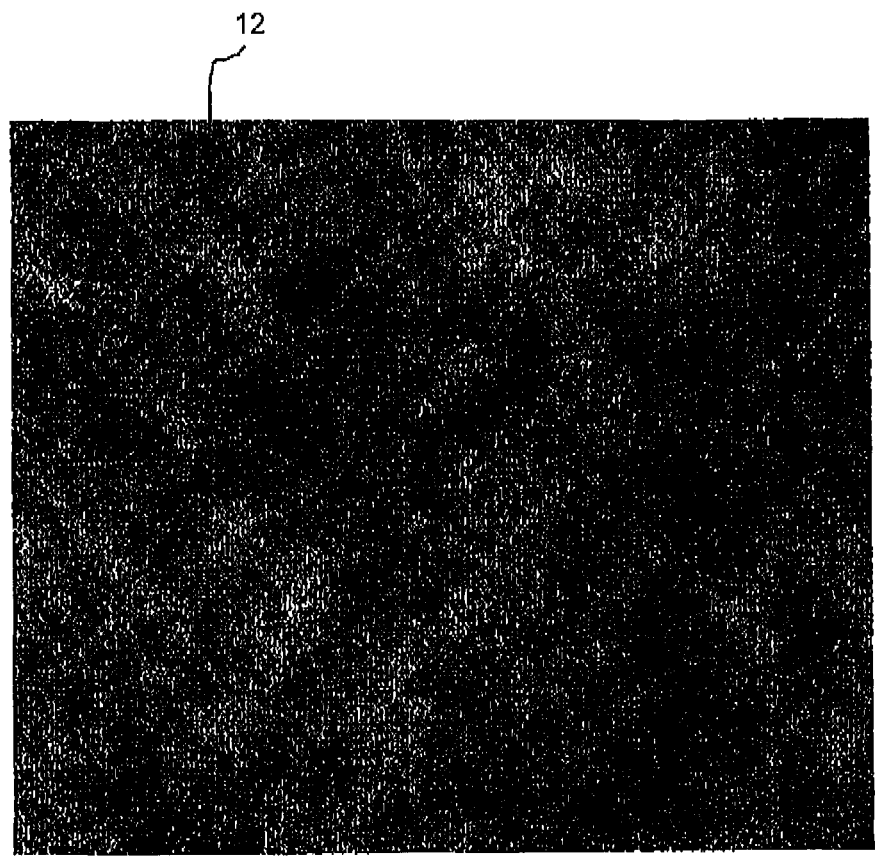
FIG. 4 is an enlarged view of a top sheet of the active composition delivery system of FIG. 1, to illustrate its texture.

Good results have been obtained by using Pellon® 541 non-woven water soluble stabilizer fabric for making the top and bottom layers 12, 14. This lightweight embroidery stabilizer (available from Patton Consumer Products, Clearwater, Florida, U.S.A.) is conventionally used to stabilize fabric during stitching, such as machine embroidery, applique, cut work, and monogramming. As can be seen in FIG. 4, which shows a preferred embodiment of a top layer 12 (the bottom layer 12 appearing the same), the surface has a perforated fibrous texture, which gives the active composition delivery system 10 a pleasing look and feel, akin to the look and feel of a conventional laundry dryer sheet, rather than the unpleasant plastic-like, often tacky feel of a laundry detergent pod or plastic-encased laundry detergent tablet. It should be noted that the image in FIG. 4 is enlarged and over-exposed to show its texture, Under normal lighting and without magnification, the top layer 12 shown in FIG. 4 appears as a soft, white material.

A preferred water soluble thread is a Tex-40 weight PVA thread.

The water-soluble material used to make the top and bottom layers 12, 14, as well as the water-soluble thread used to make the joined edges 18, the tight stitches 22, and the loose stitches 26, may be white, or coloured, to provide a desired look for the active composition delivery system 10.

The choice of active composition 16 will of course depend on the intended use of the active composition delivery system 10.

For example, the active composition 16 may be a cleaning composition, configured for cleaning things such as, for example, body parts (i.e. personal care products), dishes and utensils, and hard surfaces.

As another example, the active composition 16 may be a treatment composition, configured for treating fabric to provide, for example, scent properties (i.e. scent enhancement), fabric softening properties, anti-microbial properties, anti-bacterial properties, anti-fungal properties, insect repellant properties, scent properties, and combinations thereof.

Preferably, the active composition 16 will be anhydrous, or have a sufficiently low water content so as not to dissolve the top and bottom layers 12, 14. As such, the active composition may be in the form of a powder, a gel, a hydrophobic liquid, or a sticky composition. All such embodiments are comprehended by the present invention.

In view of the above description, it will now be understood that the preferred active composition delivery system 10 is configured so as to dissolve completely and release all of the active composition 16 it contains, when contacted with a sufficient amount of water consistent with its intended use.

Preferably, the active composition delivery system 10 may be sized, shaped, and configured for a particular use. By way of example, for use in a household washing machine (not shown), the active composition delivery system 10 may be provided in the form of a laundry detergent article 10 containing a pre-measured unit dose of a cleaning composition 16, in powder form, comprising a laundry detergent. The laundry detergent article 10 contains the powder cleaning composition 16 inside a pouch 20 formed between the water-soluble top and bottom layers 12, 14, which are sealed together along their edges 18, to keep the laundry detergent powder 16 from spilling out. By way of example only, the laundry detergent article 10 may be rectangular, appearing substantially as shown in FIG. 1, having a length of 13 cm, a width of 5 cm, and a thickness of for example, 1/18 inch to 3/8 inch. Advantageously, a laundry detergent article 10 having those dimensions may have a ratio of a) laundry detergent powder weight, to b) the weight of the PVA material containing the laundry detergent powder 16 that is fairly high, typically being 15:1 or higher. Therefore, the percent of active composition 16 may be configured to be 90% or higher for a active composition delivery system 10, according to an embodiment of the present invention.

By limiting the maximum thickness 32 of the pouch 20 and controlling the distribution of the laundry detergent powder 16 within the pouch 20 using the water-soluble loose stitches 26, the laundry detergent article 10 may be provided in a form resembling a flat sheet, which is aesthetically pleasing, and easy to handle. However, unlike known dissolvable laundry sheets, laundry detergent articles 10 according to the present invention may contain higher amounts of active cleaning composition 16 per square inch, enabling more effective cleaning with substantially the same form factor (or the same level of cleaning in a smaller form factor).

Additionally, by limiting the maximum thickness 32 of the pouch 20 and controlling the distribution of the laundry detergent powder 16 within the pouch 20 using the water-soluble loose stitches 26, the laundry detergent article 10 may deliver its active cleaning composition 16 contents more rapidly and uniformly in the washing machine. It has been found that by controlling the distribution of the laundry detergent powder 16, and maintaining an overall flat form of the laundry detergent article 10 with the water-soluble loose stitches 26 helps to keep the laundry detergent powder 16 spread out over a large surface area, which tends to increase dissolution, and at the same time reduces the type of clumping of the laundry detergent powder 16, which tends to cause uneven dissolution.

Although embodiments of the active composition delivery system 10 of the present invention include laundry detergent articles, as mentioned above, the invention is not limited thereto, but comprehends other applications, depending on the formulations of the active composition 16, the top and bottom layers 12, 14, and the water-soluble stitches 22, 26 comprised by the cleaning composition delivery system 10.

For example, other embodiments of the present invention may include active composition delivery systems 10, wherein the active composition 16 is a cleaning composition, configured for cleaning body parts (i.e. personal care products), for cleaning dishes and utensils, and for cleaning hard surfaces. All such embodiments are comprehended by the present invention.

As another example, other embodiments of the present invention may include active composition delivery systems 10, wherein the active composition 16 is a treatment composition, configured for treating fabric to provide, for example, scent properties (i.e. scent enhancement), fabric softening properties, anti-microbial properties, anti-bacterial properties, anti-fungal properties, Insect repellant properties, scent properties, and combinations thereof. All such embodiments are comprehended by the present invention.

Figure 5:
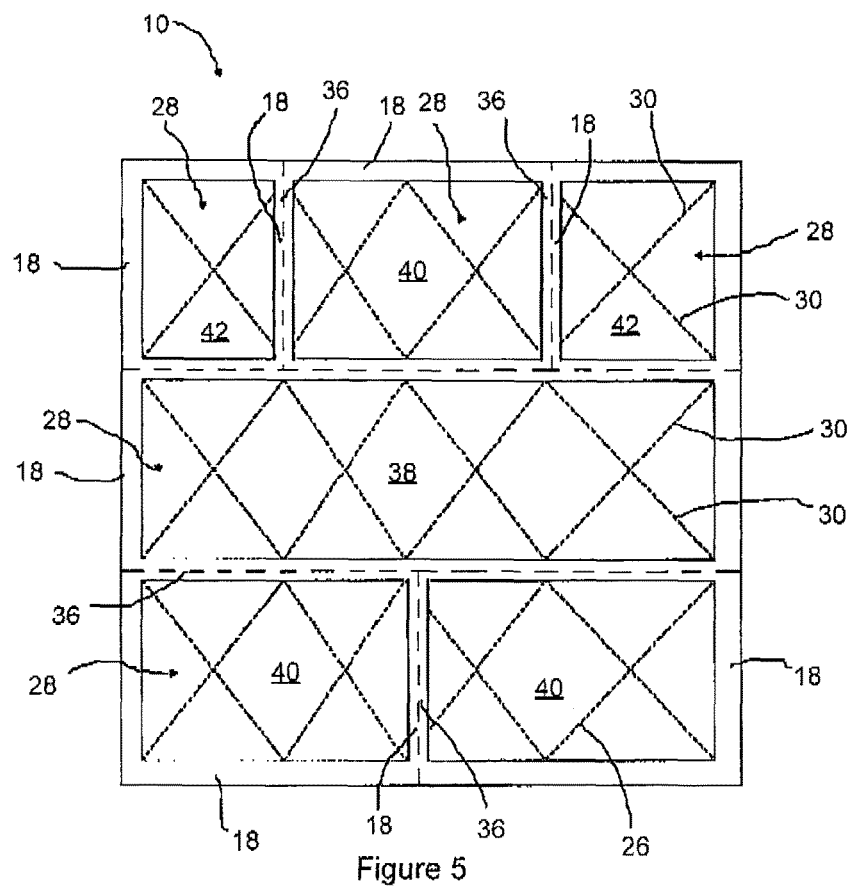
FIG. 5 is a top view of an active composition delivery system according to another embodiment of the present invention.
Figure 6:
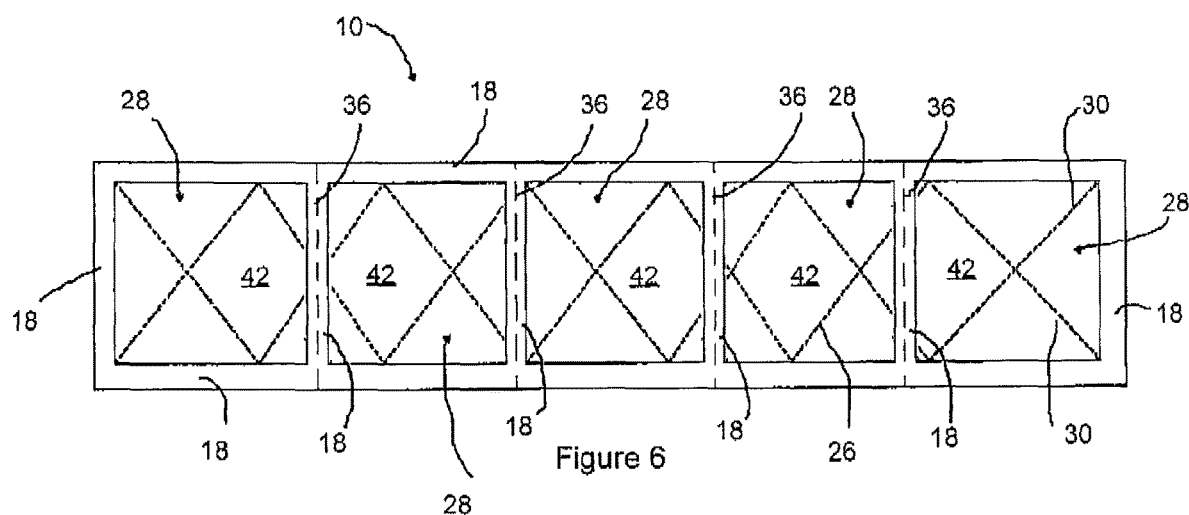
FIG. 6 is a top view of an active composition delivery system according to another embodiment of the present invention.

Referring now to FIGS. 5 and 6, the active composition delivery system 10 may include a plurality of pouches 20 joined together at their joined edges 18. The size and shape of each pouch 20 may be the same, or alternately, the active composition delivery system 10 may include differently sized, and/or shaped pouches 20. For example, differently sized, and/or shaped pouches 20 may be included to provide different pre-measured unit doses for the user to select. As another example, the pouches 20 may be configured to allow the user to easily select a combination of pre-measured unit doses for a particular application. Most preferably, the active composition delivery system 10 may be provided with a frangible member, or line of weakness 36 along some or all of the joined edges 18 separating the pouches 20 from one another, to make it easier for the user to separate and remove one or more pouches 20 from the article composition delivery system 10, so they may be used. Preferably, the frangible member/line of weakness 36 may be in the form of a line of perforations, cuts, partial cuts, or thinner material.

By way of example, the active composition delivery system 10 shown in FIG. 5 is in the shape of a square and contains six pouches 20, that may be separated along the lines of weakness 36 by a user. It will be appreciated that the active composition delivery system 10 may contain more or fewer such pouches 20. The active composition delivery system 10 shown includes a full load pouch 38, three half load pouches 40, and two quarter load pouches 42, that may be used individually, or in combination. For example, two half load poaches 40 may be good for one application, such as for example washing a full load of laundry. Similarly, two quarter load pouches 42 may be good for a partial application, such as for example washing a half load of laundry. Similarly, a quarter load pouch 42 together with a half load poach 40 may be good for a partial application, such as for example, washing a three-quarter load of laundry. And so on.

By way of another example, the active composition delivery system 10 shown in FIG. 6 is in the shape of a strip containing five pouches 20, that may be separated along the lines of weakness 36 by a user. It will be appreciated that the active composition delivery system 10 may contain more or fewer such pouches 20.

Furthermore, it Is contemplated that the active composition delivery system 10 may contain many such pouches 10 rolled up to allow for easier dispensing. In this example, the pouches 20 have the same dimensions. For example, the pouches 20 may each be good for a partial application, such as for example washing a quarter load of laundry. Accordingly, a user would be able to sever between one and four pouches 20 from the roll depending on whether the size of the load of laundry that needed washing represented a quarter load, a half load, a three-quarter load, ora full load.

Figure 7:
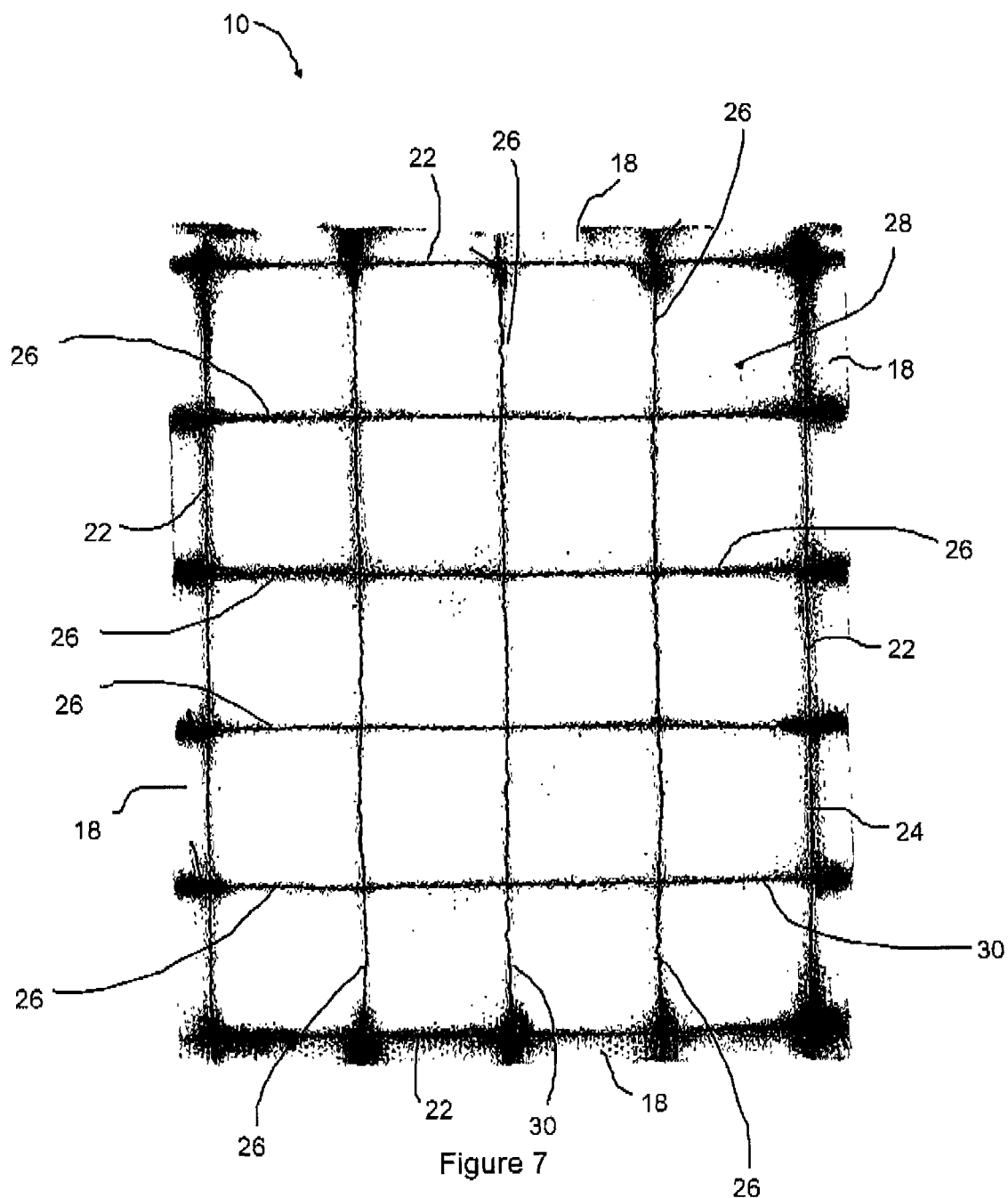
FIG. 7 is a top view of an active composition delivery system according to another embodiment of the present invention.

FIG. 7 shows an active composition delivery system 10 according to another embodiment of the present invention. In this example, the active composition delivery system 10 has a rectangular shape, and contains a pre-measured unit dose of a powder cleaning composition 16. The water-soluble PVA top and bottom layers 12, 14 are joined together at their edges 18 by sewing with PVA thread using sufficiently tight stitches 22, arranged in a continuous thread path 24 to ensure that the active composition 16 does not spill or leak out of the pouch 20 through spaces between the top and bottom layers 12, 14. The PVA thread has similar dissolution properties to those of the top and bottom layers 12, 14.

Additionally, the active composition delivery system 10 also includes a plurality of loose stiches 26 configured and arranged in the region 30 to limit a maximum thickness 32 of the active composition delivery system 10, so that it will have a generally flat, quilted profile. The plurality of loose stitches 26 are arranged in a plurality of crossing thread paths 30 to form a quilted pattern of squares. In this example, the water-soluble PVA thread has a different colour than the colour of the top and bottom layers 12, 14, so that It stands out.

FIG. 8 shows an active composition delivery system 10 according to another embodiment of the present Invention. In this example, the active composition delivery system 10 has a rectangular shape, and contains a pre-measured unit dose of a powder cleaning composition 16. The water-soluble PVA top and bottom layers 12, 14 are joined together at their edges 18 by sewing with PVA thread using sufficiently tight stitches 22, arranged in a continuous thread path 24 to ensure that the active composition 16 does not spill or leak out of the pouch 20 through gaps between the top and bottom layers 12, 14. The PVA thread has similar dissolution properties to those of the top and bottom layers 12, 14.

Additionally, the active composition delivery system 10 also includes a plurality of loose stiches 26 configured and arranged in the region 30 to limit a maximum thickness 32 of the active composition delivery system 10, so that it will have a generally flat, quilted profile. The plurality of loose stitches 26 are arranged in a plurality of crossing thread paths 30 to form a quilted pattern of squares. In this example, the water-soluble PVA thread has the same colour as the colour of the top and bottom layers 12, 14, so that it blends in.

Having described embodiments of the active composition delivery system 10 of the present invention, a method for making the same is described next.

According to one embodiment of the present invention, the active composition delivery system 10 is made by a two-stage process.

In a first-stage of the two-stage process, a continuous vertical form-fill-seal method Is used to make a train of pouches, each containing a pre-measured amount of active composition 16. In this continuous vertical form-fill-seal method, a pair of water-soluble sheets of PVA material (or a single folded over sheet of water-soluble PVA material) are joined together along their edges to form a tube, and the bottom of the tube is closed with a transverse joint to form a first pouch below a hopper. As will be appreciated, the joined edges and the transverse joints may be formed by, for example, heating, ultrasonic welding, solvent gluing, or sewing with water-soluble PVA thread. These joined edges and transverse joints become the joined edges 18 of the active composition delivery system 10, described above.

Active composition 16, such as laundry detergent powder is then added to the first pouch through the hopper, and the tube is closed with a transverse joint above the first pouch to form a second pouch below the hopper. Active composition 16 is then added to the second pouch, and the tube is again closed with a transverse joint above the second pouch to form a third pouch below the hopper. The process may be repeated several times to form a train of pouches filled with active composition 16.

The second stage of the two-stage process will now be described with reference to FIG. 9. Preferably, the train 44 of pouches 20 filled with active composition 16 proceeds from the first stage along a horizontal conveyor. As shown, the train 44 is passed below a roller 46 and proceeds in the direction of arrow 48. The roller 46 is free to move vertically according to its own weight, and is configured to ensure that the active composition 16 is evenly distributed with the pouches 20. Although only one roller 46 is shown, a plurality of rollers may be provided next to each other to ensure even distribution of the pouches 20. Alternately, or in addition to the roller(s) 46, vibration may be used to ensure the even distribution. As the train 44 continues to be carried by the conveyor in the direction of arrow 46, it will pass through a pair of synchronized sewing machines 50 which oscillate back and forth transversely across the pouches 20 in the direction of arrows 52, to form mirrored zig-zag thread paths 30 which result In a quilted pattern. In a final step (not shown), a cutting device may be configured to cleave the train 44 at each transverse joint, to form the active composition delivery system 10 comprising one pouch 20. Alternately, the final step (not shown), may be configured to a) provide a line of weakness 36, such as a line of user tearable perforations in every transverse joint, and b) cutting the train 44 at every other predetermined number of transverse joints (i.e. every sixth transverse joint), to form active composition delivery system 10 comprising more than one pouch 20 (i.e. five pouches as shown in FIG. 6), which are severable from each other by the user.

Preferably, the sewing machines 50 may be configured to travel back and forth a distance equal to the width between the Joined edges 18, synchronized to each other, as well as the conveyor moving the train 44 underneath the sewing machines 50.

Advantageously, embodiments of the active composition delivery system 10 comprehends many manners of use. For example, the active composition delivery system 10 may be configured to enable the user to prepare a volume of a cleaning or treating solution for current use or for later use. For example, the user may dissolve an active composition delivery system 10 in a pail of water and use the solution In the pail together with a mop to clean the floor. As another example, the user may dissolve an active composition delivery system 10 in a kitchen sink filled with a volume of water and use the solution to wash dishes. As yet another example, the user may hold an active composition delivery system 10 in his hands under running water to cleanse his hands, and/or other body parts. As yet another example, the user may hold an active composition delivery system 10 in her hands or on her head in the shower to shampoo or condition her hair. As yet another example, the user may dissolve an active composition delivery system 10 in a spray bottle filled with a volume of water and use solution to clean hard surfaces. As yet another example, the user may dissolve an active composition delivery system 10 in a disposable or reusable storage bottle filled with a volume of water and later dispense the solution, on an as needed basis, to use as a liquid fabric softener, a liquid dish detergent, a liquid laundry detergent, or the like.

Accordingly, the active composition delivery system 10 lends itself to uses relating to cleaning or treating people, animals, or things.

Accordingly, the active composition delivery system 10 of the present invention is not limited to the specific examples described herein to illustrate the invention, but comprehends other uses and applications, depending on the formulations of the active composition, the top and bottom water-soluble layers, and the water-soluble joints comprised by the cleaning composition delivery system, as will be recognized by persons skilled.

While reference has been made to various preferred embodiments of the invention other variations, implementations, modifications, alterations and embodiments are comprehended by the broad scope of the appended claims. Some of these have been discussed in detail In this specification and others will be apparent to those skilled in the art. For example, the loose stitches 26 in the region 28 between the joined edges 18 may be replaced with tight stitches 22, thereby removing the gaps 34. Those of ordinary skill in the art having access to the teachings herein will recognize these additional variations, implementations, modifications, alterations and embodiments, all of which are within the scope of the present invention, which invention is limited only by the appended claims.

The invention claimed is:

1. An active composition delivery system comprising:
   at least one water-soluble sheet arranged and joined together to form at least one pouch having a top layer and a bottom layer, and being surrounded by joined edges;
   an active composition disposed in said at least one pouch; and
   water-soluble thread forming a plurality of spaced apart, water-soluble joints between said top and bottom layers, said water-soluble joints being numbered and arranged in a region surrounded by said joined edges to limit a maximum thickness of said at least one pouch, and wherein said water-soluble joints are configured to allow a gap between the top and bottom layers at said water-soluble joints to control distribution of the active composition within the at least one pouch, wherein said active composition delivery system has a flat, sheet-like shape when dry, and dissolves when contacted with a sufficient amount of water, thereby releasing said active composition.

2. The active composition delivery system as claimed in claim 1, wherein said at least one water-soluble sheet comprises polyvinyl alcohol (PVA).

3. The active composition delivery system as claimed in claim 1, wherein said joined edges are formed by heating, ultrasonic welding, solvent gluing, or sewing with a water-soluble thread, said top and bottom layers together at said joined edges.

4. The active composition delivery system as claimed in claim 3, wherein said water-soluble thread is a water-soluble PVA thread.

5. The active composition delivery system of claim 1, wherein said active composition is water-soluble; and
   wherein said active composition delivery system is dissolvable in said sufficient amount of water.

6. The active composition delivery system of claim 1, wherein said active composition is water insoluble.

7. The active composition delivery system of claim 6, wherein said active composition comprises an encapsulated fragrance.

8. The active composition delivery system of claim 1, comprising a pair of said water-soluble sheets arranged and joined together to form said at least one pouch, wherein one of said pair of said water-soluble sheets forms said top layer, and the other of said pair of said water-soluble sheets forms said bottom layer.

9. The active composition delivery system of claim 1, wherein said at least one water-soluble sheet is folded over itself to form a first fold-over portion and a second fold-over portion; and
   wherein said first fold-over portion forms said top layer, and said second fold-over portion forms said bottom layer.

10. The active composition delivery system of claim 1, wherein said maximum thickness of said at least one pouch is from about 0.32 cm to about 0.95 cm, inclusive.

11. The active composition delivery system as claimed in claim 1, wherein said water-soluble thread is a water-soluble PVA thread.

12. The active composition delivery system of claim 1, wherein said water-soluble joints are arranged to define one or more paths inside said region.

13. The active composition delivery system of claim 12, wherein said one or more paths zig-zag.

14. The active composition delivery system of claim 13, wherein at least two of said zig-zagging paths are arranged to form a quilted pattern.

15. The active composition delivery system of claim 14, wherein said quilted pattern comprises triangles, squares, diamonds, rectilinear shapes, non-rectilinear shapes, or combinations thereof.

16. The active composition delivery system of claim 1, wherein said gaps are about 0.16 cm or less.

17. The active composition delivery system of claim 1, wherein said water-soluble thread has a colour that is either the same as a colour of said at least one water-soluble sheet, or different from said colour of said at least one water-soluble sheet.

18. The active composition delivery system of claim 1, wherein said active composition is a cleaning composition.

19. The active composition delivery system of claim 18, wherein said cleaning composition is formulated for cleaning human or animal body parts, dishes, drinking vessels, eating utensils, or hard surfaces.

20. The active composition delivery system of claim 1, wherein said active composition is a fabric treatment composition.

21. The active composition delivery system of claim 20, wherein said fabric treatment composition is formulated for treating fabric to provide scent properties, fabric softening properties, anti-microbial properties, anti-bacterial properties, anti-fungal properties, insect repellant properties, scent properties, or combinations thereof.

22. The active composition delivery system of claim 1, wherein said active composition does not prematurely dissolve said top and bottom layers.

23. The active composition delivery system of claim 22, wherein said active composition is a powder, a gel, a hydrophobic liquid, or a sticky composition.

24. The active composition delivery system of claim 1, wherein said at least one water-soluble sheet is arranged and joined together to form a plurality of said pouches surrounded by said joined edges; and
wherein each said pouch is attached to one or more adjacent pouches by one or more of said joined edges.

25. The active composition delivery system of claim 24, wherein all of said pouches have the same size and shape; and
wherein all of said pouches contain the same pre-measured dose of said active composition.

26. The active composition delivery system of claim 25, wherein said same pre-measured dose corresponds to one of a full application or treatment, and a partial application or treatment.

27. The active composition delivery system of claim 26, wherein said partial application or treatment comprises a quarter of said full application or treatment, a half of said full application or treatment, or a three-quarters of said full application or treatment.

28. The active composition delivery system of claim 25, wherein at least one of said pouches has a first size or a first shape; and
wherein at least one of said pouches has a second size which is different from said first size, or a first shape which is different from said first shape.

29. The active composition delivery system of claim 28, wherein said first size or said first shape corresponds to a different pre-measured unit dose of said active composition, as compared to said second size or said second shape.

30. The active composition delivery system of claim 29, wherein said first size or said first shape corresponds to one of a full application or treatment, and a partial application or treatment; and
wherein said second size or said shape corresponds to the other of said full application or treatment, and said partial application or treatment.

31. The active composition delivery system of claim 30, wherein said partial application or treatment comprises a quarter of said full application or treatment, a half of said full application or treatment, or a three-quarters of said full application or treatment.

32. The active composition delivery system of claim 24, further comprising one or more lines of weakness in said joined edges to allow a user to separate one or more of said pouches from said plurality of said pouches.

33. The active composition delivery system of claim 32, wherein each of said one or more lines of weakness is a line of perforations, a line of cuts, a line of partial cuts, a line of thinner joined edge, or a combination thereof.

34. The active composition delivery system of claim 24, wherein said plurality of said pouches are arranged one after the next in the shape of a strip.

35. The active composition delivery system of claim 34, wherein said strip is rolled up in a roll.

36. The active composition delivery system of claim 35, wherein said strip is configured for use with an automatic dispenser in a washing machine.

37. The active composition delivery system of claim 24, wherein said plurality of said pouches are arranged as a rectangle or a square.

38. A method for making an active composition delivery system, comprising using a water-soluble thread to join together at least one water-soluble sheet arranged to form at least one pouch having a top layer and a bottom layer, and being surrounded by joined edges;
wherein the water-soluble thread forms a plurality of spaced apart, water-soluble joints between said top and bottom layers, said water-soluble joints being numbered and arranged in a region surrounded by said joined edges to limit a maximum thickness of said at least one pouch, and
wherein said water-soluble joints are configured to allow a gap between the top and bottom layers at said water-soluble joints to control distribution of an active composition with the at least one pouch.

39. The method of claim 38,
wherein said active composition delivery system has a flat, sheet-like shape when dry, and dissolves when contacted with a sufficient amount of water, thereby releasing said active composition.

* * * * *